United States Patent
Nakauchi et al.

(10) Patent No.: US 6,582,905 B1
(45) Date of Patent: Jun. 24, 2003

(54) TRANSMEMBRANE TRAPPING METHODS

(76) Inventors: Hiromitsu Nakauchi, 429-3, Ohi, Kukizakimachi, Inashiki-gun, Ibaraki 300-1243 (JP); Yukio Nakamura, 4-22-1-203, Matsushiro, Tsukuba-shi, Ibaraki 305-0035 (JP); Sousuke Miyoshi, 2-25-10-404, Matsushiro, Tsukuba-shi, Ibaraki 305-0035 (JP); Dong ku Kim, 1-2-302, Kasuga, Tsukuba-shi, Ibaraki 305-0821 (JP)

( * ) Notice: Subject to any disclaimer, the term of this patent is extended or adjusted under 35 U.S.C. 154(b) by 0 days.

(21) Appl. No.: 09/230,378

(22) PCT Filed: Jul. 18, 1997

(86) PCT No.: PCT/JP97/02502
§ 371 (c)(1),
(2), (4) Date: Mar. 15, 1999

(87) PCT Pub. No.: WO98/03645
PCT Pub. Date: Jan. 29, 1998

(30) Foreign Application Priority Data

Jul. 23, 1996 (JP) .............................. 8/192644

(51) Int. Cl.$^7$ ................................. C12Q 1/68
(52) U.S. Cl. .................... 435/6; 435/DIG. 6; 435/69.1; 935/11
(58) Field of Search ............................. 536/23.4, 23.1, 536/18.7; 435/489, 6, DIG. 6, 69.1; 935/11

(56) References Cited

U.S. PATENT DOCUMENTS

| 5,767,336 A | * | 6/1998 | Skarnes | 800/2 |
| 5,976,834 A | * | 11/1999 | Sathe et al. | 435/69.1 |
| 6,020,157 A | * | 2/2000 | Bergsma et al. | 435/69.1 |
| 6,060,249 A | * | 5/2000 | Baker et al. | 435/6 |

FOREIGN PATENT DOCUMENTS

EP     0 607 054     7/1984

OTHER PUBLICATIONS

Science, vol. 261, pp. 600–603, Jul. 30, 1993.
Proc. Natl. Acad. Sci. USA, vol. 84, pp. 3365–3369, May 1987.
B. M. J. Foxwell, et al., Clinical and Experimental Immunology, vol. 90, pp. 161–169, "Cytokine Receptors: Structure and Signal Transduction", 1992.
Robert D. Klein, et al., Proceedings of the National Academy of Sciences of USA, vol. 93, No. 14, pp. 7108–7113, "Selection for Genes Encoding Secreted Proteins and receptors", Jul. 9, 1996.

* cited by examiner

*Primary Examiner*—Andrew Wang
*Assistant Examiner*—Tomas Friend
(74) *Attorney, Agent, or Firm*—Oblon, Spivak, McClelland, Maier & Neustadt, P.C.

(57) ABSTRACT

The present invention provides a method of cloning a protein coding for a membrane protein without the need of using anyantibody or ligand.

The method of cloning a membrane protein comprises selecting a protein having a signal sequence, using a DNA coding for the signal sequence and N-terminal sequence of the protein as the reporter gene, and screening for a gene for a protein having a transmembrane domain(s).

The present invention is concerned also with the CDNA obtained by using such method, a vector containing the DNA, a transformant as transformed with the vector, and the transcription product of the DNA as produced by the transformant.

14 Claims, 1 Drawing Sheet

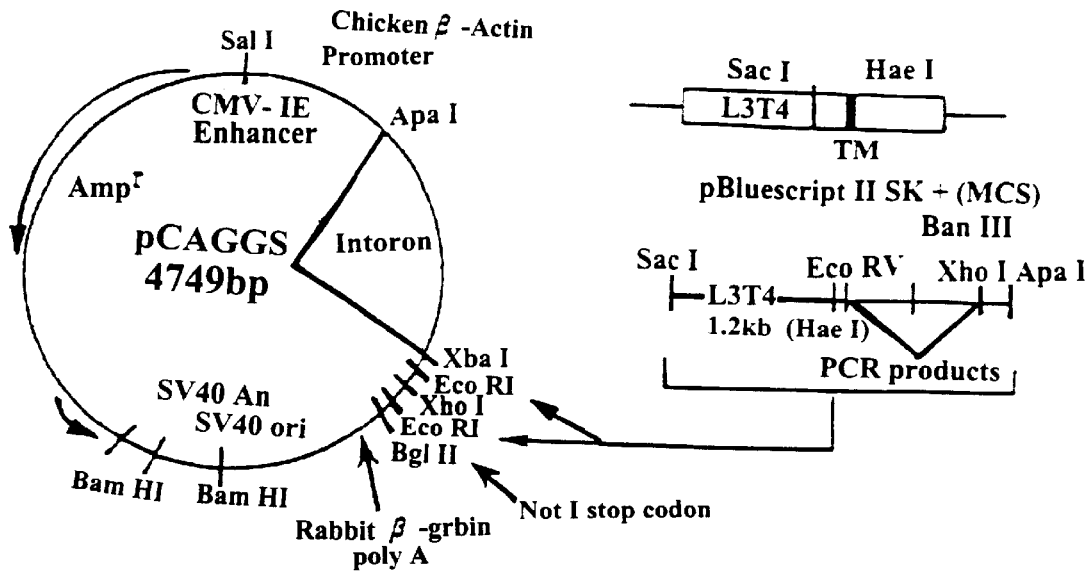# Transfection
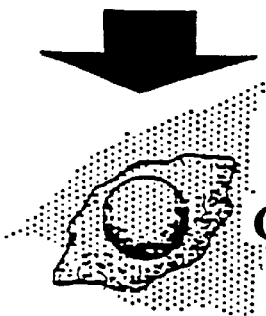
FACS analysis
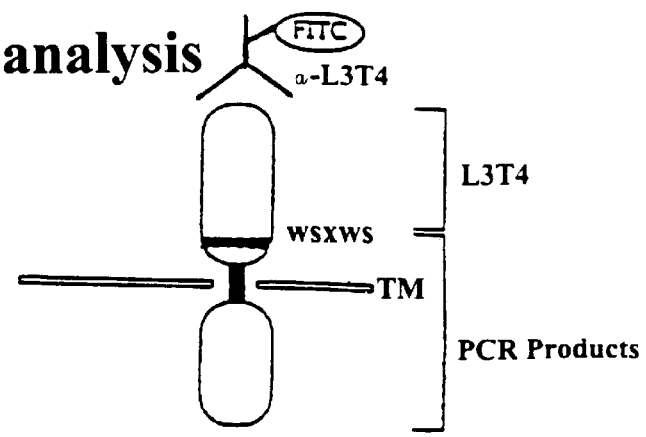

SEQUENCE LISTING

<160> NUMBER OF SEQ ID NOS: 8

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence:synthetic DNA
<223> OTHER INFORMATION: N at positions 31, 32, 33, and 34 can be A, C, G, OR T

<400> SEQUENCE: 1
cctctgaagg ttccagaatc gatactcgag nnnngg                              36

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:synthetic DNA
<223> OTHER INFORMATION: N at position 6 may be C or T
<223> OTHER INFORMATION: N at position 7 may be C or G
<223> OTHER INFORMATION: N at position 8 may be A or C
<223> OTHER INFORMATION: N at position 9 may be C or G
<223> OTHER INFORMATION: N at position 15 may be C or T

<400> SEQUENCE: 2
tggagnnnnt ggagn                                                     15

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:synthetic DNA

<400> SEQUENCE: 3
cctctgaagg ttccagaatc gatag                                          25

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:synthetic DNA
<223> OTHER INFORMATION: N at position 6 may be C or T
<223> OTHER INFORMATION: N at position 9 may be A, C, G, or T

<400> SEQUENCE: 4
tggagngant ggagt                                                     15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:synthetic DNA
<223> OTHER INFORMATION: N at position 6 may be C or T
<223> OTHER INFORMATION: N at position 9 may be A, C, G, or T

<400> SEQUENCE: 5
tggagngant ggagc                                                     15

```
<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:synthetic
      DNA
<223> OTHER INFORMATION: N at position 6 may be C or T
<223> OTHER INFORMATION: N at position 7 may be A, C, G, or T

<400> SEQUENCE: 6
tggagnncct ggagt                                                    15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:synthetic
      DNA
<223> OTHER INFORMATION: N at position 6 may be C or T
<223> OTHER INFORMATION: N at position 9 may be A, C, G, or T

<400> SEQUENCE: 7
tggagnaant ggagt                                                    15

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence:synthetic
      DNA
<223> OTHER INFORMATION: N at position 6 may be C or T
<223> OTHER INFORMATION: N at position 7 may be A, C, G, or T

<400> SEQUENCE: 8
tggagnncct ggtc                                                     14
```

TRANSMEMBRANE TRAPPING METHODS

BACKGROUND OF THE INVENTION

Field of the Invention

In the mechanisms of differentiation and proliferation of cells, membrane proteins expressed on the surface of said cells have a very important biological significance. Cytokine, peptide hormone or neurotransmitter receptors, cell adhesion molecules and the like are involved in signal transduction from cell to cell. The present invention relates to a method of cloning proteins coding for such membrane proteins without requiring any antibody or ligand at all. More particularly, it relates to a method of cloning proteins having transmembrane domains.

DESCRIPTION OF THE BACKGROUND

The methods most widely used at present for cloning membrane molecules include several improvements or modifications of the expression (or phenotype) cloning method designed in 1987 by Seed and Aruffoi (Proc. Acad. Sci. USA, 84:3365-3369, 1987). They comprise utilizing, for example, transient expression by Cos7 cells and an expression vector containing the replication origin of SV40, thus introducing a cDNA library constructed using an expression vector for use in animal cells into Cos7 cells, and thereby causing expression of a cDNA library-derived membrane protein on the cell surface. Cells in which the desired target membrane molecule is expressed are concentrated by panning or by means of a FACS, using an antibody to or a ligand of said membrane molecule, and the plasmid DNA is recovered and used again to transfect Cos7 cells, and this concentration procedure is repeated (panning method or sorting method, respectively). Another method comprises dividing an expression vector cDNA library into a certain number of small groups, introducing each group into Cos7 cells, detecting membrane molecule expression using an isotope-labeled antibody or ligand, dividing the positive group or groups further into small groups each comprising a small number of plasmids, and repeating the transfection to attain cloning (sib selection method).

However, the methods mentioned above each is effective only when the antibody to or the ligand of the target membrane molecule expressed on the cell surface is clearly known. On the contrary, the present method is an epoch-making one which enables cloning of a membrane molecule on cells without requiring any antibody or ligand at all. The fact that no antibody or ligand is required is very advantageous in that intracellular signal transduction substances can be cloned while avoiding troublesome establishment of assay systems in which a biological activity is used as an indicator. Further, in the case of cytokine receptors, the level of expression on the cell surface is very low (several hundreds to several thousands per cell) and, therefore, it is difficult to prepare monoclonal antibodies which are to be obtained through immunization with a solublized cell fraction. In addition, it is practically impossible to make approaches by the conventional method based on amino acid sequence determination following protein purification. Unlike the conventional methods, the present method is a novel one which enables even cloning of quite novel membrane molecules the ligand of which has never been identified.

DETAILED DESCRIPTION OF THE PREFERRED EMBODIMENTS

The present invention consists in a method of cloning a DNA coding for a membrane protein which comprises the steps of:

A) selecting a protein having a signal sequence, and preparing a DNA (reporter gene) coding for the signal sequence and N terminal sequence of said protein;

B) constructing a DNA library containing a DNA coding for a target membrane protein;

C) constructing an expression vector by joining the DNA library obtained in B) above to the downstream of the reporter gene obtained in A) above;

D) transforming an appropriate host with the expression vector obtained in C) above, and selecting cells in which the reporter gene is expressed on the cell surface; and E) recovering the vector from the positive cells obtained to give a clone containing a part or the whole of the DNA coding for the target membrane protein; and F) when the DNA obtained in E) above codes only for a part of the target protein, obtaining a complete DNA clone based on the sequence thereof.

The present invention also relates to the cDNA obtained by using these methods, a vector containing said DNA, a transformant resulting from transformation with said vector, and the product of transcription of said DNA as produced by said transformant.

The present inventors revealed that even a membrane molecule which is quite new and an antibody to which can hardly be prepared or any ligand of which has not yet been identified can be cloned by using the method of the present invention.

In the following, the cloning method of the present invention is fully described step by step.

A) First of all, a protein having a signal sequence is selected, and a DNA (reporter gene) coding for the signal sequence and N-terminal sequence of said protein is prepared. The signal sequence-containing protein is such a protein as to permeate through the membrane and includes, among others, membrane proteins and secretory proteins. As the reporter gene, there may be mentioned, for example, a DNA obtained by selecting a known membrane protein and depriving a DNA coding for, said membrane protein of the transmembrane domain-encoding region and the downstream thereof. Said known membrane protein is not limited to any particular protein provided that the nucleotide sequence coding therefor is already known (for example, the cDNA sequence for said protein is known, or the chromosome DNA sequence is known) and thus the transmembrane domain(s) thereof can be estimated and that the expression thereof on the membrane surface can be confirmed. It is, however, preferred that it be a homologous protein (for example, if the novel membrane protein to be cloned (target membrane protein) is a mammal-derived one, the known membrane protein should be also a mammal-derived one). As specific examples of such known membrane protein, there may be mentioned known mammalian cell-surface antigens, such as murine L3T4, human CD4 and human HLA antigens, and various receptor proteins occurring on the cell surface, such as receptor type tyrosine kinase, receptor type serine/threonine kinase and cytokine receptors. A DNA corresponding to one derived from the DNA coding for such a known membrane protein by deletion of the transmembrane domain(s) and the downstream thereof is prepared by utilizing an ordinary genetic engineering technique (e.g. DNA synthesis, restriction enzyme cleavage of cDNA followed by purification, etc.).

B) A DNA library containing a DNA coding for the target membrane protein is then constructed. The DNA library containing a DNA coding for the target membrane protein may be a cDNA library or a chromosomal DNA library. The DNA library can be constructed by an ordinary method used in genetic engineering. For example, if a novel membrane protein expressed in hepatocytes is the target membrane protein, mRNA is collected from hepatocytes. If a novel membrane protein expressed in brain cells is the target membrane protein, mRNA is obtained from brain cells. Then, cDNA is produced using a reverse transcriptase and further converted to the corresponding double-stranded molecule using a DNA polymerase. A cDNA library is constructed by inserting said double-stranded molecule into an appropriate vector (e.g. plasmid or phage) A commercially available DNA library may also be used. When it is intended to obtain a cDNA for a membrane protein of a particular family gene origin, it is advantageous to use a cDNA library concentrated by degenerated PCR utilizing a consensus sequence such as a motif sequence, which occurs in the family genes.

C) And, an expression vector is constructed with the DNA of the DNA library obtained in B) above joined to the downstream of the reporter gene obtained in A) above. As specific examples of the vector to be used in constructing such expression vector, there may be mentioned pCD (Okayama et al., Mol. Cell. Biol., 3:280, 1983), pCD-SR (Takebeet, Mol. Cell. Biol., 8:466, 1988), pCDM 8 (Funakoshi), pBMG, pEF, pMAM (Toyobo) and the like. The expression vector is constructed by ligating the reporter gene and the DNA of the library containing a target membrane protein-encoding DNA, or a DNA derived therefrom by random hydrolysis, in that order, to the downstream of the promoter occurring in such a vector. When a CDNA sequence concentrated by degenerated PCR utilizing a consensus sequence is used, the cDNA can be joined in advance to the reporter gene without reading frame shifting.

D) An appropriate host is transformed with the expression vector obtained in C) above, and cells expressing the reporter gene on the membrane surface are selected. When the DNA coding for the transmembrane domain(s) in the DNA library is one encoding a fusion protein with a known membrane protein, said fusion protein is trapped on the cell membrane and the cells are rendered positive to an antibody against the epitope of the known membrane protein on the host cell membrane surface. In the case of a cDNA which does not code for any transmembrane domain, the fusion protein with a known membrane protein is not hold on the cell membrane, namely it is a secretory protein, hence it is not stained with an antibody against the known membrane protein. Therefore, by selecting cells binding to an antibody against the known membrane protein, it is possible to select those cells transformed with the expression vector containing a cDNA coding for the whole or part of the target membrane protein. In cases where the target membrane protein is of an animal cell origin, for instance, animal cells are preferred as the host cells. For example, such hosts as COS7, which can realize transient expression, are preferred. For selecting cells expressing the reporter gene on the membrane surface, the panning method, which utilizes an antibody against the reporter protein, or the sorting method using a FACS or the like is used, among others. These procedures for transformation, expression and selection may be repeated several times, as necessary, whereby the transformant (positive cells) expressing the target membrane protein can be concentrated.

E) The vector is recovered from the positive cells obtained to give a clone containing a part or the whole of the DNA coding for the target membrane protein. Where necessary, the base sequence of a fragment coding for the target membrane protein is determined and the sequence of the target membrane protein is analyzed or searched for using an analysis software of GENETYX (SOFTWARE-KAIHATSUGAISYA (software development company)), for instance, to determine whether the desired DNA has been cloned.

F) When the DNA obtained in E) above encodes only a part of the target membrane protein, a full DNA clone is obtained from a DNA library such as a cDNA library or a chromosomal DNA library on the basis of the sequence thereof.

BRIEF DESCRIPTION OF THE DRAWING

FIG. 1 is a schematic representation of an embodiment of the transmembrane trapping method of the present invention.

BEST MODES FOR CARRYING OUT THE INVENTION

The following examples illustrate the present invention in further detail. In the examples, the procedures described in Molecular Cloning: A Laboratory Manual (Maniatis et al. , Cold Spring Harbor Laboratory, 1983) were fundamentally followed unless otherwise specified.

EXAMPLE 1

Preparation of Total RNA

Thus, $1 \times 10^7$ Ba/F3 cells (RIKEN Cell Bank, Cell No. RCB0805) were washed with two portions of phosphate buffer. After removal of the supernatant by centrifugation, 1 ml of ISOGEN (Nippon Gene) was added to the pellet and, after thorough stirring, the suspension was allowed to stand at room temperature for 5 minutes. Chloroform (0.2 ml) was added to the suspension and, after thorough stirring, the mixture was allowed to stand at room temperature for 3 minutes and then centrifuged at 5,000 rpm at 4° C. for 15 minutes. The aqueous phase was recovered, 0.5 ml of 2-propanol was added thereto, and the mixture was stirred, then allowed to stand at room temperature for 10 minutes and centrifuged at 15,000 rpm at 4° C. for 15 minutes. The supernatant was removed, 1 ml of 0.75% ethanol was added to the precipitation and, after stirring, the mixture was again centrifuged at15,000 rpm at 4° C. for 5 minutes. After removal of the supernatant, the ethanol was eliminated and then 20 µl of water was added to give a total RNA solution.

EXAMPLE 2 mRNA Preparation mRNA preparation was performed using the Quick prep maicro mRNA purification kit (Pharmacia) according to the manual attached thereto.

(1) To 20 µl of the whole RNA solution obtained in Example 1 was added 0.4 ml of Extraction buffer, followed by further addition of 0.8 ml of Elution buffer. The mixture was stirred and then centrifuged at 15,000 rpm at 4° C. for 10 seconds.

(2) Separately, 1 ml of oligo(dT) beads were taken and centrifuged at 15,000 rpm at 4° C. for 10 seconds. The supernatant was removed, 1.2 ml of the supernatant obtained in 2–1 above was added to the pellet and the whole was gently stirred for 3 minutes.

(3) The preparation was centrifuged at 15,000 rpm at 4° C. for 10 seconds, the supernatant was removed, 1 ml of High-salt buffer was added, and the mixture was stirred. This procedure was repeated five times.

(4) Using Low-salt buffer in lieu of High-saltbuffer, the procedure of (3) was repeated two times.

(5) The preparation was transferred to the attached column and centrifuged at 15,000 rpmat 4° C. for 5 seconds. Further, the procedure comprising adding 0.5 ml of Low-salt buffer to the column and the subsequent centrifugation was repeated three times.

(6) To the column was added 0.2 ml of Elution buffer at 65° C. and centrifugation was performed at 15,000 rpm at 4° C. for 5 seconds for elution of mRNA. This procedure was repeated two times.

(7) To the eluate were added 40 μl of 3 M sodium acetate and 10 μl of glycogen, the mixture was stirred and, after further addition of 1 ml of 99.5% ethanol, the mixture was allowed to stand at −20° C. for an hour.

(8) After 15 minutes of centrifugation at 15,000 rpm at 4° C., the supernatant was completely removed to give mRNA.

EXAMPLE 3 cDNA Synthesis cDNA synthesis was carried out using the Superscript preamplification system (GIBCO BRL) according to the manual attached thereto. Thus, (1) 11 μl of DEPC-water and 1 μl of 30 μM 5'-UNI-XhoI random primer were added to the mRNA, and the mixture was incubated at 70° C. for 10 minutes, immediately followed by 1 minute of standing on ice.

5'-UNI-XhoI random primer (SEQ ID NO:1 in the sequence listing)

5'-CCT-CTG-AAG-GTT-CCA-GAA-TCG-ATA-CTC-GAG-[N][N][N]-[N]GG-3'

-UNI sequence-XhoI- (2) To this were added 2 μl of 0.1 M dithiothreitol (DTT) solution, 2 μl of 25 mM magnesium chloride (MgCl) solution, 2 μl of 10×reverse transcriptase buffer (RTase buffer) and 1 μl of 10 mM dNTP solution, and the mixture was allowed to stand at room temperature for 5 minutes. Then, 1 μl of reverse transcriptase (SuperScript II) was added and the reaction was carried out at room temperature for 10 minutes and further at 42° C. for 50 minutes.

(3) There action was terminated at 70 over 15minutes. Then, 1 μl of E. coli ribonuclease H (RNase H) was added, and the reaction was carried out at 37° C. for 20 minutes.

EXAMPLE 4

Polymerase Chain Reaction (PCR)

The following PCR conditions were used and the reaction was initiated by the hot start method.

PCR Conditions 30 seconds at 94° C., 30 seconds at 60° C. and 90 seconds at 72° C.; 30 cycles PCR Solution

| | |
|---|---|
| 2.5 mM dNTP | 8 μl |
| 10 × Buffer | 10 μl |
| 5' Primer | 1 μl |
| 3' Primer | 1 μl |
| Water | 78 μl |
| Template DNA | 1 μl |

-continued

| | |
|---|---|
| Taq polymerase | 1 μl |
| Total | 100 μl |

PCR Primers

WSXWS degenerated primer (SEQ ID NO:2)
  5'-TGG-AG(C/T)-(C/G)(A/C)(C/G)-TGG-AG(C/T)

UNI primer (SEQ ID NO:3)
  5'-CCT-CTG-AAG-GTT-CCA-GAA-TCG-ATA-G

EXAMPLE 5

Insert CDNA Preparation (1) The PCR product obtained in Example 4 was purified by desalting, primer elimination and so on using the Wizard PCR peps resin (Promega) and eluted with 50 μl of water.

(2) To 50 μl of this DNA solution were added 1 μl of 25 mM dNTP, 6 μl of 10×Buffer and 1 μl of T4 DNA polymerase and, further addition of water to make 60 μl, the reaction was carried out at 37° C. for 15 minutes.

(3) The reaction mixture was desalted and purified with the Wizard DNA purification resin (Promega), and the DNA was eluted with 50 μl of water.

(4) To this solution were added 1 μl of XhoI (restriction enzyme) and 6 μl of 10×Buffer and, after further addition of water to make 60 g 1, the reaction was carried out at 37° C. for 60 minutes.

(5) The reaction mixture was desalted and purified using the Wizard DNA purification resin, and the DNA was eluted with 20 μl of water.

EXAMPLE 6

Vector DNA Preparation (1) The SacI-HaeI region of the murine L3T4 cDNA as deprived of the transmembrane domain downstream was inserted into the cloning vector pBluescript II (Toyobo) at the multicloning site SacI-SmaI site.

(2) This was excised at the SacI-ApaI, then rendered blunt-ended by T4 DNA polymerase treatment, and inserted into pCAGGS (Gene, 108 (1991), 193–200), which is an expression vector for use in animal cells, at the EcoRI cleavage site rendered blunt-ended (pCAGGS-L3T4) (cf. FIG. 1).

(3) The restriction enzymes EcoRV and XhoI (1 μl each) and 5 μl of 10×Buffer were added to 2 μl of the pCAGGS-L3T4 vector and, after further addition of water to make 50 μl, the reaction was carried out at 37° C. for 1 hour.

(4) The reaction mixture was electrophoresed on a low-melting agarose gel, and the vector band was excised and allowed to stand at 68° C. for 10 minutes.

(5) The DNA was purified using the Wizard PCR peps resin and eluted with 20 μl of water.

EXAMPLE 7

Ligation Reaction (1) The insert DNA (9 μl) was mixed with 1 μl of the vector DNA, then 10 μl of Ligation reaction medium I (Ligation Kit Ver. 2, Takara Shuzo) was added, and the reaction was carried out at 16° C. for 30 minutes.

(2) The reaction mixture was desalted and purified using the Wizard DNA purification resin. The DNA was eluted with 20 μl of water.

EXAMPLE 8

Large-scale cDNA Preparation (1) The DNA (2 µl) was added to 48 µl of competent *Escherichia coli* DH10B, the mixture was transferred to a Gene Pulser cuvette (Bio-Rad, 1 mm), and electro-poration was performed at 1.25 kV, 400Ω and 25 µl FD, immediately followed by addition of 1 ml of SOB solution at 37° C. The mixture was transferred to a 15-ml tube and shaken at 37° C. for 1 hour for effecting transformation.

(2) The culture fluid obtained above was added to 200 ml of LB medium, and shake-culture was conducted overnight at 37° C.

(3) *E. coli* cells were collected by 10 minutes of centrifugation at 6,000 rpm at 40° C., and the CDNA was then recovered by the cesium chloride method.

EXAMPLE 9

Transfection (1) 6-Well dishes were sown with 1×10⁶ Cos7 cells per well, and cultivation was carried out overnight on DMEM medium (GIBCO).

(2) The DNA (5 µl g) was mixed with 100 µl of Opti-MEM medium (GIBCO). Separately, 100 µl of Opti-MEM medium and 5 µl of Lipofectin (GIBCO) were mixed together. Both mixtures were combined and the resulting mixture was allowed to stand at room temperature for 30 minutes.

(3) To this was added 800 µl of Opti-MEM medium, the mixture was poured onto Cos7 cells washed twice with Opti-MEM medium, and cultivation was conducted for 8 hours.

(4) The culture fluid was subjected to medium exchange for DMEM, followed by 2 days of further cultivation.

EXAMPLE 10

FACS Sorting

FACS sorting was carried out basically according to the manual attached to a FACS device (Vantage, Vecton Dickinson). Cell staining was performed fundamentally according to "Men'eki Kenkyuu no Kiso Gijutsu (Basic Techniques for Immunological Studies)" (edited by Seishi Kozu and Shinsuke Taki, publsihed by Yodosha)

(1) 1 ml of 5 mM EDTA-PBS solution was added to each well of the 6-well dishes and allowed to stand at room temperature for 10 minutes and, then, the Cos7 cells were peeled off from the dishes by pipetting.

(2) The cells were washed with 5% FCS-PBS and then centrifuged at 1,500 rpm at room temperature for 5 minutes, the supernatant was removed, 1 p 1 of FITC-labeled anti-L3T4 monoclonal antibody (Pharmingen) was added to the pellet, and the mixture was allowed to stand on ice for 30 minutes.

(3) After washing with two portions of 5% FCS-PBS solution, the supernatant was removed, the cells were suspended in 1 mg/ml propidium iodide-PBS solution, and L3T4 (FITC) positive cells were sorted out using a FACS (Vantage, Vecton Dickinson).

EXAMPLE 11

Hirt Extraction (1) The cells sorted out were centrifuged at 5,000 rpm at 4° C. for 5 minutes, the supernatant was removed, 0.4 ml of 0.6% SDS-10 mM EDTA solution was added and, after 15 minutes of standing at room temperature, 0.1 ml of 5 M aqueous sodium chloride solution was added, and the mixture was allowed to stand overnight on ice.

(2) After 30 minutes of centrifugation at 15,000 rpm at 4° C., the supernatant was recovered and subjected to phenol-chloroform extraction, followed by further ethanol precipitation. The DNA precipitate was dissolved by adding 5 µl of water.

EXAMPLE 12

Concentration of positive cells was effected by repeating the procedures of Examples 8 to 11 three times.

EXAMPLE 13

Base Sequence Determination (1) The plasmid DNA was recovered from the concentrated positive cells by the Hirt extraction method, *Escherichia coli* was transformed therewith and sown onto LB plates.

(2) A single colony was picked up from one of the plates, and the plasmid DNA was recovered by the alkali method and purified with the Wizard DNA purification resin.

(3) The cycle sequencing dye terminator method (Perkin Elmer) was performed and the DNA nucleotide sequence was determined on an automated nucleotilde sequencer (Applied Biosystems model 373A).

(4) The DNA nucleotide sequence determined was subjected to homology searching consulting with the Gen-Bank. As a result, the DNA obtained was found to code for interleukin 3 receptor.

EXAMPLE 14

The design of the WSXWS degenerated primer utilizing the WSXWS motif was modified and the procedures of Examples 1 to 13 were followed using F36P cells (RIKEN Cell Bank, Cell No. RCB0775), namely a human IL-3- or human GM-CSF-dependent human leukemia cell line.

As a result, the KH97 (IL-3Rβ unit) gene could be efficiently cloned using primer (1) and, further, the IL-2Rγ, IL-4Rα and IL-6Rα genes could be efficiently cloned using primer (2), the GM-CGFRα gene using primer (3), the IL-13Rα gene using primer (4), and the EpoR gene using primer (5).

ps WSXWS Degenerated Primers (1) 5'-TGG-AG(C/T)-GAN-TGG-AGT (SEQ ID NO:4)
(2) 5'-TGG-AG(C/T)-GAN-TGG-AGC (SEQ ID NO:5)
(3) 5'-TGG-AG(C/T) -NCC-TGG-AGT (SEQ ID NO:6)
(4) 5'-TGG-AG(C/T)-AAN-TGG-AGT (SEQ ID NO:7)
(5) 5'-tgg-ag(c/t)-ncc-tgg-tc (seq id no:8)

What is claimed is:

1. A method of cloning DNA coding for a target transmembrane protein, which comprises:
   a) selecting a known membrane protein comprising a signal sequence, an N-terminal sequence, and a transmembrane domain;
   b) preparing a reporter gene coding for the signal sequence and the N-terminal sequence of said membrane protein by elimination of the transmembrane domain and downstream thereof;
   c) constructing a DNA library comprising the DNA coding for a target transmembrane protein;
   d) constructing an expression vector by joining the DNA library obtained in c) to the downstream of the reporter gene obtained in b);
   e) transforming a host with the expression vector obtained in d);
   f) selecting cells in which the reporter gene is expressed on the cell surface;
   g) recovering the expression vector from the positive cells obtained to give a clone comprising a part or the whole of the DNA coding for a target transmembrane protein; and
   h) determining the DNA sequence of the expression vector obtained in g).

2. The method of claim 1, wherein the known membrane protein is a mammalian cell-surface antigen protein.

3. The method of claim 1, wherein the known membrane protein is murine L3T4.

4. The method of claim 1, wherein the known membrane protein is human CD4.

5. The method of claim 1, wherein the known membrane protein is selected from the group of human HLA antigens.

6. The method of claim 1, wherein the known membrane protein is a receptor protein occurring on mammalian cell surfaces.

7. The method of claim 6, wherein the receptor protein is receptor tyrosine kinase.

8. The method of claim 6, wherein the receptor protein is serine/threonine kinase.

9. The method of claim 6, wherein the receptor protein is selected from the group consisting of cytokine receptors.

10. The method of claim 1, wherein the DNA library in step c) is a cDNA library.

11. The method of claim 1, wherein the DNA library in step c) is a chromosomal DNA library.

12. The method of claim 1, wherein said expression vector in step d) is constructed by ligating the reporter gene and the DNA of the library comprising a target membrane protein encoding DNA, or a DNA obtained therefrom by random hydrolysis to downstream of a promoter of said vector.

13. The method of claim 1, wherein in step e) the cells in which the reporter gene is expressed on the cell surface are selected by detecting an antibody against the reporter protein.

14. The method of claim 1, wherein the known membrane protein is of an animal cell, and the host is an animal cell.

* * * * *